United States Patent
Aelen et al.

(10) Patent No.: US 9,554,730 B2
(45) Date of Patent: Jan. 31, 2017

(54) PHYSIOLOGICAL SENSOR

(71) Applicant: KONINKLIJKE PHILIPS N.V., Eindhoven (NL)

(72) Inventors: Paul Aelen, Eindhoven (NL); Pierre Hermanus Woerlee, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 33 days.

(21) Appl. No.: 14/394,937

(22) PCT Filed: May 1, 2013

(86) PCT No.: PCT/IB2013/053437
§ 371 (c)(1),
(2) Date: Oct. 16, 2014

(87) PCT Pub. No.: WO2013/164768
PCT Pub. Date: Nov. 7, 2013

(65) Prior Publication Data
US 2015/0094617 A1    Apr. 2, 2015

Related U.S. Application Data

(60) Provisional application No. 61/641,351, filed on May 2, 2012.

(51) Int. Cl.
*A61B 5/103*    (2006.01)
*A61B 5/107*    (2006.01)
*A61H 31/00*    (2006.01)

(52) U.S. Cl.
CPC ............ *A61B 5/107* (2013.01); *A61B 5/1036* (2013.01); *A61H 31/005* (2013.01);
(Continued)

(58) Field of Classification Search
CPC ...................................................... A61B 5/107
(Continued)

(56) References Cited

U.S. PATENT DOCUMENTS 4,077,400 A    3/1978  Harrigan
7,122,014 B2   10/2006 Palazzolo et al.
(Continued)

FOREIGN PATENT DOCUMENTS

CN    102164573 A    8/2011
CN    102341085 A    2/2012
(Continued)

*Primary Examiner* — Michael C Stout
*Assistant Examiner* — Nicholas E Kolderman

(57) ABSTRACT

According to the invention, a compression depth sensor for measuring a compression depth comprises a first pressure transducer (30), attachable to a fixed element, a first liquid filled lumen (20), having a first fixed lumen end (21) attachable to the pressure transducer and a first movable lumen end (22) being movable between a first position and a second position, a distance between the first and second position defining the compression depth, whereby the first pressure transducer is adapted to measure the compression depth by measuring a change in liquid pressure in the lumen during movement of the first movable lumen end between the first position and the second position. A CPR apparatus according to the invention comprises such a compression sensor.

12 Claims, 5 Drawing Sheets

(52) U.S. Cl.
CPC ......... *A61H 31/006* (2013.01); *A61H 31/007* (2013.01); *A61H 2201/5071* (2013.01)

(58) Field of Classification Search
USPC ........................................................ 600/587
See application file for complete search history.

(56) References Cited

U.S. PATENT DOCUMENTS

| | | | |
|---|---|---|---|
| 8,876,742 B2 | 11/2014 | Centen | |
| 2002/0177793 A1* | 11/2002 | Sherman | ............... A61H 31/00 601/41 |
| 2004/0082888 A1* | 4/2004 | Palazzolo | .......... A61B 5/04012 601/41 |
| 2008/0208082 A1 | 8/2008 | Nysaether et al. | |
| 2010/0040217 A1 | 2/2010 | Aberg et al. | |
| 2010/0228165 A1* | 9/2010 | Centen | ................. A61H 31/004 601/41 |
| 2010/0228166 A1 | 9/2010 | Centen | |
| 2012/0083720 A1* | 4/2012 | Centen | ................. A61H 31/005 601/41 |

FOREIGN PATENT DOCUMENTS

| | | |
|---|---|---|
| FR | 2842900 A1 | 1/2004 |
| WO | 0215836 A2 | 2/2002 |
| WO | 2010009531 A1 | 1/2010 |
| WO | 2011011633 A2 | 1/2011 |
| WO | 2011058001 A1 | 5/2011 |

\* cited by examiner

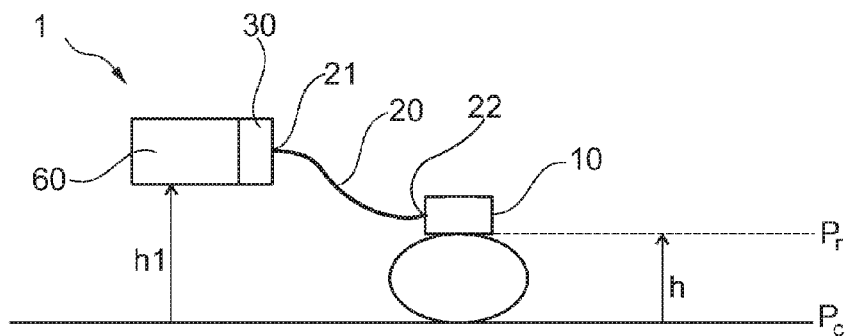
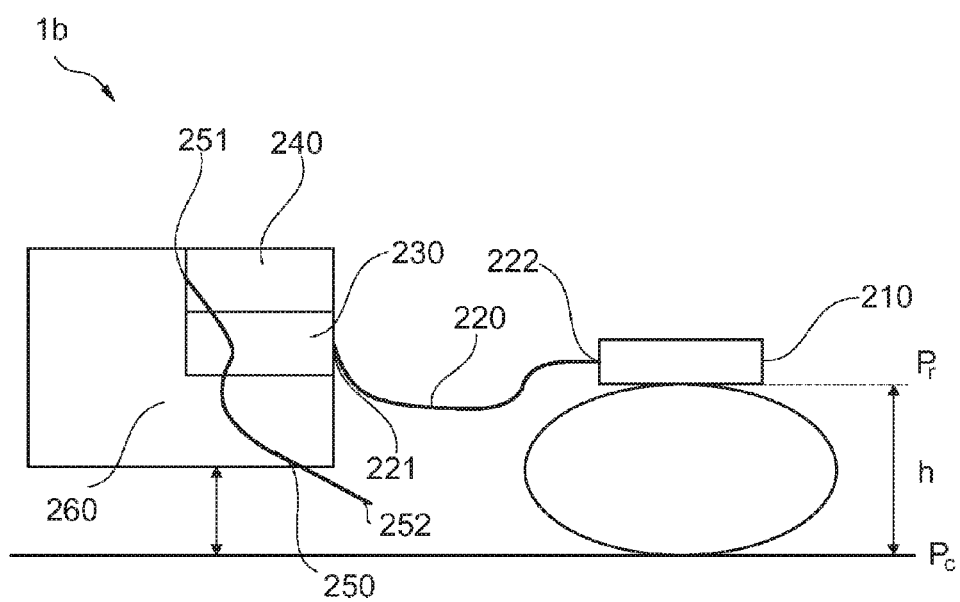

PHYSIOLOGICAL SENSOR

FIELD OF THE INVENTION

The invention relates to the field of cardiopulmonary resuscitation. The invention addresses a physiological sensor and a cardiopulmonary resuscitation apparatus comprising a physiological sensor, and a method for sensing a physiological parameter.

BACKGROUND OF THE INVENTION

Cardiopulmonary resuscitation (CPR) is a well-known technique for increasing the chance for survival from cardiac arrest. However, it is very difficult to perform manual cardiopulmonary resuscitation with consistent high quality.

Since CPR quality is key for survival, there is a strong drive to have a mechanical automated device to replace less reliable and long duration manual chest compressions. Automated CPR (A-CPR) apparatuses are adapted to apply standard compressions to the patient.

It is obvious that tailoring the chest compressions to the patient is beneficial. In places where there is no ACPR device available, it is also useful to give rescuers feedback on their manual CPR performance. The CPR performance value is often given by deviation to a target depth and a target frequency of the compressions. Typically, the target depth is around 5.0 cm and the target frequency is around 100 compressions per minute.

The frequency of the compressions is generally measured by measuring the time between compression peaks. Sensors devices have been developed, to give feedback on the achieved compression depth. The known sensor devices are based on either a spring or an accelerometer based measurement, to measure the relative compression depth.

However, the known sensor devices suffer several drawbacks. With standard accelerometer based compression depth measurements, an important error is made when a patient is laying on a compliant surface, such as a standard mattress. Because of the chest compressions, both the patient and the compliant surface are compressed on the same time, effects that are both measured with the accelerometer. The amount the compliant surface is compressed can be up to half the amount the chest is compressed. Therefore an accelerometer based compression depth of 5 cm, can be only +−3 cm when not corrected for the compliant surface. Standard correction is not possible because it is not known beforehand if resuscitation is happening on a hard or compliant surface. Further, the amount of compliant surface compression depends on the surface itself, the absolute weight of the patient, the weight distribution, etc, which makes determining the correction factor impossible It would be desirable to achieve a compression sensor which is adapted to measure an absolute compression height, in particular chest compression height.

It would be desirable to achieve a compression sensor that is adapted to measure the actual compression depth that is administered to a patient.

It would be desirable to achieve a cardio pulmonary apparatus with a compression sensor that is adapted to measure the actual compression depth that is administered to a patient.

SUMMARY OF THE INVENTION

To better address one or more of these concerns, the present invention proposes a compression depth sensor for measuring a compression depth, the sensor comprising a first pressure transducer, attachable to a fixed element, a first liquid filled lumen, having a first fixed lumen end attachable to the pressure transducer and a first movable lumen end being movable between a first position and a second position, a distance between the first and second position defining the compression depth. The first pressure transducer is adapted to measure the compression depth by measuring a change in hydrostatic liquid pressure in the lumen during movement of the first movable lumen end between the first position and the second position. Hence the present invention proposes using hydrostatic pressure measurements, whereby an absolute compression depth can be obtained.

In one aspect of the invention, the first movable lumen end comprises fixation means for attachment to a first movable element. The fixation means could be positioned on any movable element whose displacement should be measured, e.g. directly on a patient's chest or on a compression pad during resuscitation.

In a further aspect of the invention, the compression depth sensor comprises a second pressure transducer, attachable to said fixed element, a second liquid filled lumen, having a second fixed lumen end attachable to the second pressure transducer and a second movable lumen end being movable between a third position and a fourth position, a distance between the third and fourth positions defining a moving height, whereby the second pressure transducer is adapted to measure the moving height by measuring the liquid pressure being in the second lumen during movement of the second movable lumen end between the third and the fourth positions, and a subtractor for deriving a difference between the first compression depth and the moving height. By providing a second pressure transducer together with a second lumen, an additional position measurement can be achieved. The additional position measurement can be used for taking account of external parameters such as changes in height of a bed during a resuscitation or transport.

The second movable lumen end may comprise second fixation means for fixation below a patient. Advantageously, the second fixation means may be useful to make an additional position measurement, depending on which application the compression sensor is used. When the compression sensor is used for sensing compression depth in the course of a resuscitation, the additional position measurements can be performed below the patient, e.g. on the surface on which the patient is laying, which can be compliant. The additional position measurement can be used to correct the compression depth measurements, by taking into account the compliance of the surface.

In a further aspect of the invention, the first pressure transducer and the second pressure transducer are one of a strain gage transducer or a tip pressure transducer.

The present invention also proposes the use of a compression depth sensor as described above, for measuring a compression depth experienced by a patient's chest during CPR.

The present invention further proposes a Cardio Pulmonary Resuscitation (CPR) apparatus, comprising a compression depth sensor, wherein the first movable element is a compression pad. In one aspect of the invention, the compression depth sensor is adapted to derive the absolute position of the compression pad.

In yet another aspect of the present invention, a method is further disclosed for measuring a compression depth, the method comprising measuring, by a first pressure transducer, attachable to a fixed element, a liquid pressure in a first liquid filled lumen, said first liquid filled lumen having a first fixed lumen end attachable to the first pressure transducer and a first movable lumen end being movable between a first position and a second position, during movement of the first movable lumen end between the first position and the second position, wherein a distance between the first and second position corresponds to the compression depth.

In yet another aspect of the present invention, the method comprises measuring, by a second pressure transducer, another pressure corresponding to a moving height by measuring a liquid pressure in a second liquid filled lumen, said second liquid filled lumen having a second fixed lumen end attachable to the second pressure transducer and a second movable lumen end being movable between a third position and a fourth position, during movement of the second movable lumen end between the third and the fourth positions.

In one aspect of the present invention, the method comprises deriving a difference between the first compression depth and the moving height. Advantageously, chest height and molding effects are measured by measuring a DC component of the differential pressure.

In a further aspect of the present invention, the method comprises positioning the first movable lumen end on a contact pad and positioning the second movable lumen end below a patient chest. Advantageously, two pressure measurements can be achieved, wherein additional effects such as chest molding or a compliant surface can be taken into account.

In yet another aspect of the present invention, the method, comprises calibrating a position of at least one of the first movable lumen end and of the second movable lumen end before a first compression.

BRIEF DESCRIPTION OF THE DRAWINGS

These and other aspects of the invention will be apparent from and elucidated with reference to the embodiment(s) described herein after, given as examples only, in which:

FIG. 1 shows schematic block diagram of a sensor apparatus according to a first aspect of the invention;

FIG. 2 shows a schematic block diagram of a sensor apparatus 1b for cardio pulmonary resuscitation according to a second aspect of the invention;

DETAILED DESCRIPTION OF THE EMBODIMENTS

Figure 3:
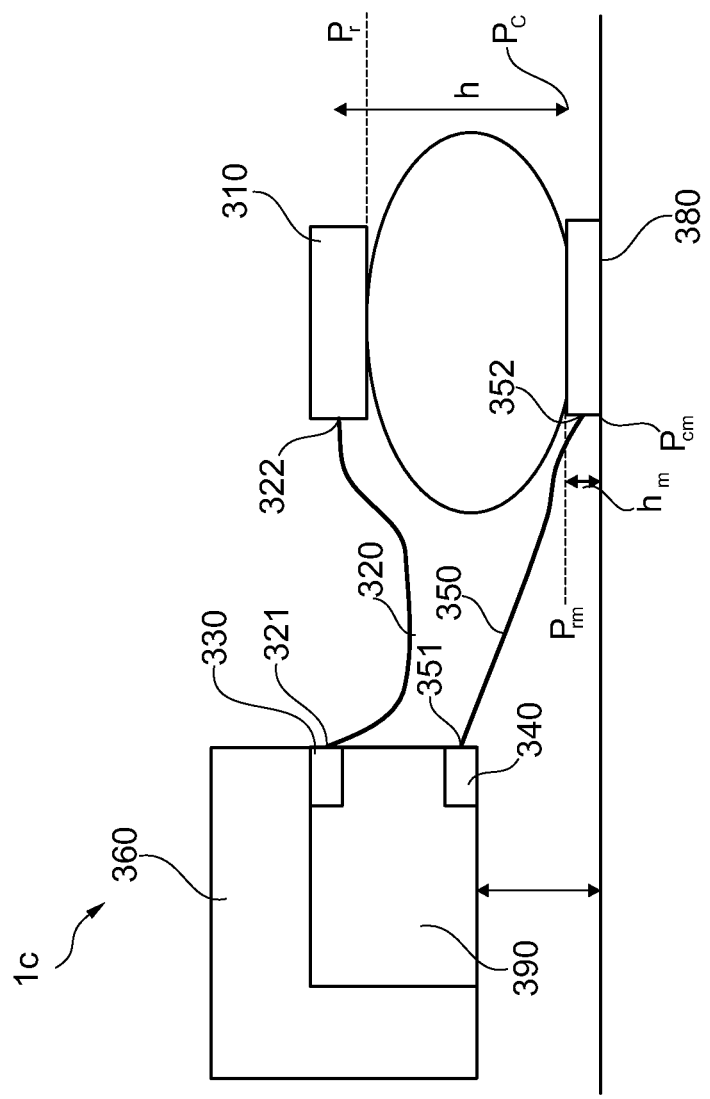
FIG. 3 shows a schematic block diagram of a sensor apparatus 1c for cardio pulmonary resuscitation according to another aspect of the invention.

FIG. 1 shows a schematic block diagram of a sensor apparatus 1 for cardio pulmonary resuscitation according to a first aspect of the invention.

The sensor apparatus 1 comprises a liquid filled lumen 20, having a first fixed lumen end 21 and a first movable lumen end 22, and a pressure transducer 30. The first fixed lumen end 21 is attached to the pressure transducer 30. The first movable lumen end 22 comprises fixation means (e.g., a suitable fixation member), for fixation to a movable element 10 (e.g., the fixation member is configured to enable the first movable lumen end to be attached to the movable element).

In the example of FIG. 1, the movable element 10 is a contact pad 10 for performing cardiopulmonary resuscitation (CPR) on a patient. The contact pad 10 may be a contact pad of an automated CPR device, or a pad designed for helping a rescuer performing CPR. Alternately, the liquid filled lumen 20 may also be attached directly on a patient's chest on which CPR is performed.

The first movable lumen end 22 is therefore moving with the chest compressions, between a first position, corresponding to a rest position Pr of the chest, and a second position, corresponding to a compressed position Pc of the chest. For a given compression, the compression depth is defined by a height h between the first and second positions.

The pressure transducer 30 in the embodiment of FIG. 1 is mounted on a patient monitor 60, at a fixed (non-moving) position.

The pressure transducer 30 is adapted to measure the compression depth by measuring the change in hydrostatic pressure in the lumen during movement of the first movable lumen end 22 of between the first and second positions. With each compression, the pressure transducer 30 is fixed whilst the first movable lumen end 22 moves. The change in hydrostatic liquid pressure is proportional to the height h between the rest position Pr and the compressed position Pc, hence proportional to the compression depth.

Advantageously, the compression depth is directly related to the measured pressure difference. The compression depth is obtained by subtracting the two pressures measured between the rest position and the compressed position of the first movable lumen end. When the sensor reference pressure is constant and sensor position is not varied, also changes in rest position can be monitored. The person skilled in the art will recognize that the absolute compression depth can be measured during the course of a resuscitation.

The pressure transducer 30 in the embodiment of FIG. 1 is mounted on a patient monitor. Of course, the pressure transducer 30 may be mounted elsewhere, as long as the pressure transducer 30 is positioned at a fixed location.

The pressure transducer 30 can be any kind of pressure transducer, e.g. a strain gage transducer, a tip pressure transducer, etc.

The person skilled in the art will readily recognize that measuring the absolute position of the chest is of great importance in taking into account chest molding effects. Chest molding relates to the fact that a patient's chest might not recoil to its original position during the course of a CPR event. Because of chest molding, the absolute position of the chest changes during CPR, which in its turn affects the compression depth.

The incomplete recoil can be a short term or a long term effect. The short term effect is caused by giving compressions faster than the ability of the chest to recoil. The long term effect is caused by the diminishing elasticity of the human chest. When the chest is compressed for a long time, the elasticity is reduced, causing the chest to recoil to a lower position than originally planned. This is comparable to stretching a rubber band (or slow foam mattress). If this is done a few times, the band will not get back to its original state, but will be stretched somewhat in its relaxed position.

In known sensor devices for measuring compression depth, such as accelerometer-based technique, the start of each new compression is defined as being the absolute zero point. Accordingly, the incomplete recoil of the chest is completely overlooked with accelerometer based position measurements. The same drawback is obtained when using any other relative position measurement based position measurements.

As will be explained later with reference to FIG. 4 the pressure signal from the pressure transducer 30 has an alternating component and continuous component. The continuous component of the pressure transducer 30 can provide information on the chest thickness and also incorporates fixed height difference between the sensor and the patient. In the course of resuscitation, the chest thickness may not recover entirely due to chest molding. The continuous component of the difference therefore drifts, between an initial level to a drift level. If the chest does not recoil completely—or in other words if the rest position changes over the course of the resuscitation, there will be a change in the DC level of the pressure. The change in DC level corresponds with change in rest level when all other components of the signal do not vary. The instantaneous compression depth is measured by the alternating component of the pressure signal. Note that when the height of the bed is changed with respect to the sensor the DC pressure component will also change.

The hardware needed for hydrostatic pressure measurements is standard equipment that is used in many applications, and will not be described in details therein.

FIG. 2 shows a schematic block diagram of a sensor apparatus 1b for cardio pulmonary resuscitation according to a first aspect of the invention.

The sensor apparatus 1b comprises a first liquid filled lumen 220 and a first pressure transducer 230.

The first liquid filled lumen 220 has a first fixed lumen end 221 and a first movable lumen end 222. The first fixed lumen end 221 is attached to the first pressure transducer 230. The first movable lumen end 222 comprises fixation means, for fixation to a movable element. In the example of FIG. 2, the first movable lumen end 222 is attached to a contact pad 210 for performing CPR.

The contact pad 210 may be a contact pad of an automated CPR device, or a pad designed for helping a rescuer performing CPR. The first movable lumen end 222 may also be attached directly on a patient's chest on which CPR is performed.

The first movable lumen end 222 is therefore movable between a first position, corresponding to a rest position Pr of the chest, and a second position, corresponding to a compressed position Pc of the chest, whilst the first fixed lumen end 221 is fixed. Hence, a height h between the first and second position defines the compression depth, for a given compression.

The first pressure transducer 230 is adapted to measure the compression depth by measuring the change in liquid pressure in the first lumen 220 during movement of the first movable lumen end 222 between the first position and the second position.

The first pressure transducer 230 in the embodiment of FIG. 2 is mounted on a patient monitor 260. Of course, the first pressure transducer 30 may be mounted elsewhere, as long as the pressure transducer 230 is positioned fixedly at an absolute height level.

The sensor apparatus 1b comprises a second pressure transducer 240 and a second liquid filled lumen 250 having a second fixed lumen end 251 and a second movable lumen end 252. The second fixed lumen end 251, in the example of FIG. 2, is fixed to the second pressure transducer 240 and the second movable lumen end 252 is fixed at a non moving location near the patient. The second pressure transducer 240 is adapted to form a reference pressure sensor, in order to measure external deviations such as changes of the atmospheric pressure and level changes of the monitoring apparatus.

The second pressure transducer 240 in the example of FIG. 2 is mounted on a patient monitor, close to the first pressure transducer 230. Of course, the second pressure transducer 240 may be mounted elsewhere, as long as the pressure transducer is positioned fixedly at an absolute height level. In another embodiment of the present invention, the second movable lumen end can be positioned below the patient's chest, in a similar position as is shown on FIG. 3.

The first and second pressure transducers 230, 240 can be one of a strain gage transducer a tip pressure transducer, or any other pressure transducer. Note that by using two different sensors, a drift in the sensors' signals poses a challenge.

FIG. 3 shows a schematic block diagram of a sensor apparatus 1c for cardio pulmonary resuscitation according to another aspect of the invention.

The sensor apparatus 1c comprises a first liquid filled lumen 320 and a first pressure transducer 330.

The first liquid filled lumen 320 has a first fixed lumen end 321 and a first movable lumen end 322. The first fixed lumen end 321 is attached to the first pressure transducer 330. The first movable lumen end 322 comprises fixation means, for attachment to a movable element 310.

In the example of FIG. 3, the first movable lumen end 322 is attached to a contact pad 310, similarly to the embodiments of FIGS. 1 and 2. The first movable lumen end 322 is therefore movable between a first position, corresponding to a rest position Pr of the chest, and a second position, corresponding to a compressed position Pc of the chest.

Hence, a height h between the first and second positions defines the compression depth, for a given compression.

The first pressure transducer 330 is adapted to measure the compression depth by measuring a liquid pressure change in the first liquid filled lumen 320 during movement of the first movable lumen end 322 between the first position and the second position. The first pressure transducer 330 in the embodiment of FIG. 3 is mounted on a patient monitor 360. Of course, the first pressure transducer 330 may be mounted elsewhere, as long as the pressure transducer is positioned fixedly at an absolute height level.

The sensor apparatus 1c comprises a second pressure transducer 340, and a second liquid filled lumen 350 having a second fixed lumen end 351 and a second movable lumen end 352. The second fixed lumen end 351, in the example of FIG. 3, is fixed to the second pressure transducer 340 and the second movable lumen end 352 is fixed under the patient, below the patient's chest, preferably on the mattress 380 where the patient is lying.

The second pressure transducer 340 is adapted to form a reference pressure sensor, in order to measure external deviations such as changes of the mattress height in the course of the resuscitation, the mattress being a compliant surface. Because of the chest compressions, both the patient and the compliant surface are compressed on the same time.

The second movable lumen end 352 is therefore movable between a third position, corresponding to a rest position Prm of the mattress, and a fourth position, corresponding to a compressed position Pcm of the mattress. Hence, a height hm between the third and fourth positions defines the change in the reference position, for a given compression.

The second pressure transducer 340 is adapted to measure the mattress compression depth by measuring a change in liquid pressure in the second liquid filled lumen 350 during movement of the second movable lumen end 352 between the third and fourth positions.

With the two pressure transducers, differential pressure measurement can be achieved, using a subtractor 390 to derive the resulting pressure as the difference between the pressure measured by the first pressure transducer and the pressure measured by the second pressure transducer. Advantageously, both the chest thickness and the real compression depth can be measured, as explained with reference to FIGS. 5A to 5C. Further, the absolute position of the first movable lumen end, hence of the compression pad, can be obtained.

The hardware needed for hydrostatic pressure measurements is standard equipment that is used in many applications, and will not be described in details therein.

Figure 4:
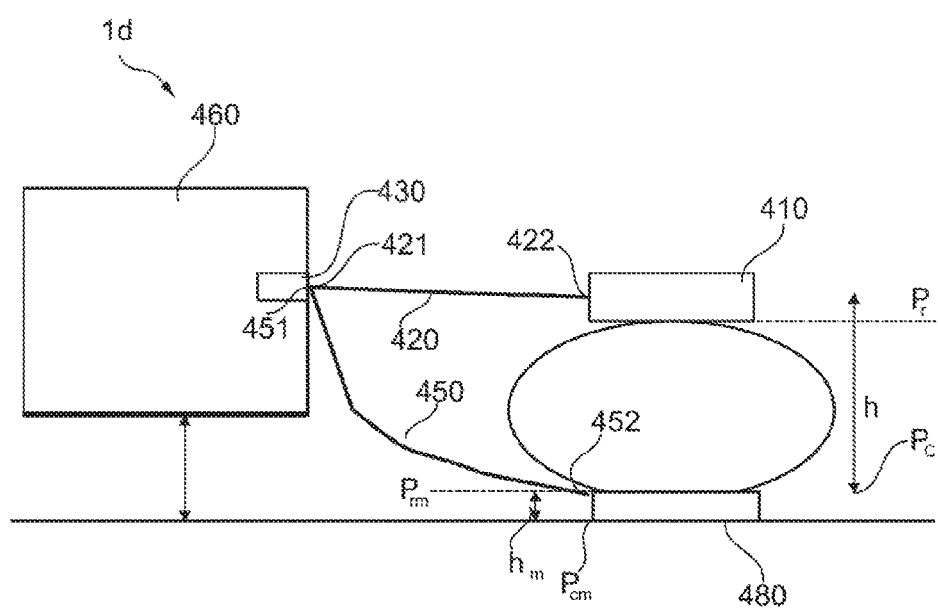
FIG. 4 shows a schematic block diagram of another sensor apparatus 1d for cardio pulmonary resuscitation according to another aspect of the invention

FIG. 4 shows a schematic block diagram of a sensor apparatus 1*d* for cardio pulmonary resuscitation according to another aspect of the invention. The sensor apparatus 1*d* of FIG. 4 mainly differs from the sensor apparatus 1*c* of FIG. 3 in that the apparatus uses a differential pressure sensor with only one transducer, mounted on patient monitor 460.

The sensor apparatus 1*d* comprises a single differential pressure transducer 430, together with two lumens 420, 450. The first liquid filled lumen 420 has a first fixed lumen end 421 and a first movable lumen end 422. The first fixed lumen end 421 is attached to the pressure transducer 430. The first movable lumen end 422 comprises fixation means, for attachment to a movable element 410, and in particular to a contact pad 410, similarly to the embodiments of FIGS. 1 and 3. The first movable lumen end 422 is therefore movable between a first position, corresponding to a rest position Pr of the chest, and a second position, corresponding to a compressed position Pc of the chest.

The second liquid filled lumen 450 has a second fixed lumen end 451 and a second movable lumen end 452. The second fixed lumen end 451 is fixed to the single differential pressure transducer 430 and the second movable lumen end 452 is fixed under the patient, below the patient's chest, preferably on the mattress 480 where the patient is lying.

The second movable lumen end 452 is therefore movable between a third position, corresponding to a rest position Prm of the mattress, and a fourth position, corresponding to a compressed position Pcm of the mattress. Hence, a height hm between the third and fourth positions defines the change in the reference position, for a given compression. A change in liquid pressure in the second liquid filled lumen 450 during movement of the second movable lumen end 452 between the third and fourth positions gives information on the mattress compression depth.

Differential pressure measurement can be achieved by the single pressure transducer which is adapted to directly obtain the differential pressure resulting from the changes measured in the first lumen and the changes measured in the second lumen. Advantageously, both the chest thickness and the real compression depth can be measured, similarly to the system described with reference to FIG. 3. Further, the absolute position of the first movable lumen end, hence of the compression pad, can be obtained. By using a single transducer, differences in drift between two transducers can be eliminated.

Figure 5A:
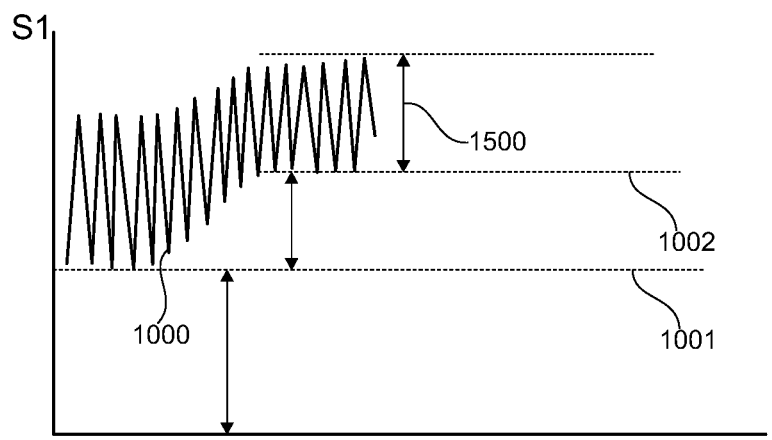
FIG. 5A is a graphical representation of a pressure signal from a first pressure transducer in a sensor apparatus of FIG. 3.
Figure 5B:
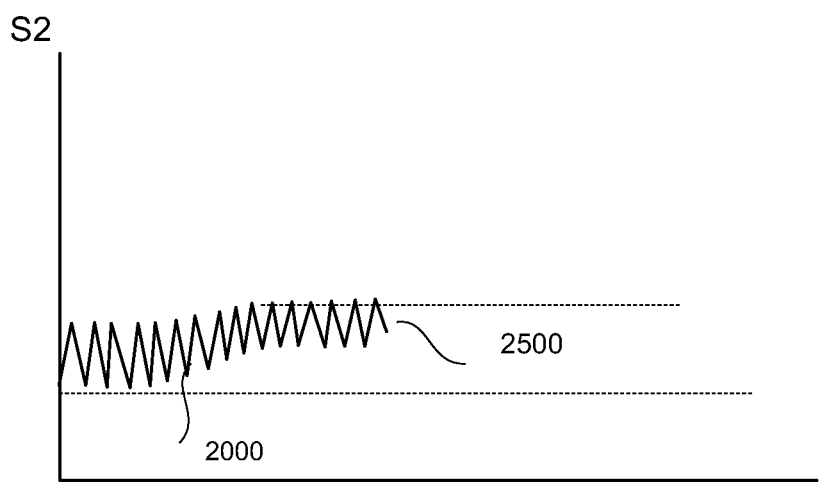
FIG. 5B is a graphical representation of the pressure signal from a second pressure transducer in a sensor apparatus of FIG. 3.
Figure 5C:
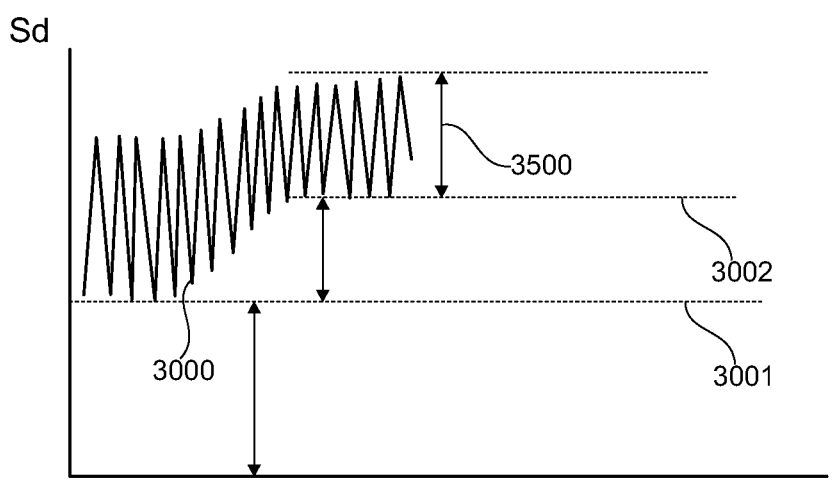
FIG. 5C is a graphical representation of a differential pressure between the pressure measured by a first pressure transducer and the pressure measured by a second pressure transducer measured over time, in a course of a resuscitation, in a sensor apparatus of FIG. 3.

FIG. 5A is a graphical representation of the pressure signal S1 from the first pressure transducer 330, FIG. 5B is a graphical representation of the pressure signal S2 from the second pressure transducer 340 and FIG. 5C is a graphical representation of the differential pressure Sd between the pressure measured by the first pressure transducer and the pressure measured by the second pressure transducer measured over time, in a course of a resuscitation, with the sensors of FIG. 3.

The pressure signals S1, S2, from the first and second transducers, 330, 340, both have a continuous component 1000, 2000 and an alternating component 1500, 2500, respectively. The differential pressure Sd therefore also has a continuous component 3000 and an alternating component 3500.

The differential continuous component 3000 can change between an initial level 3001 to a drift level 3002. The initial level 3001 provides information on the chest thickness and the difference between the initial level 3001 and the drift level 3002 of the differential continuous component 3000 between transducer 330 and 340 gives information on the chest molding. The alternating component 3500 of the differential pressure Sd provides information on the chest compression depth.

The information on the chest thickness may be used in order to tune the CPR performance to a specific person, whereby persons of different morphology may require different compression depths for a successful CPR.

The person skilled in the art will note that chest thickness measurement is achieved with embodiments wherein two lumens are used, e.g. in the example of FIG. 3 where the sensor apparatus comprises two transducers associated with two lumens or in the example of FIG. 4 wherein the sensor apparatus comprises one transducer associated with two lumens, the second movable end being below the patient. Further, measuring chest molding is achieved with a sensor apparatus comprising one or more transducer together with one or more lumen.

Figure 6:
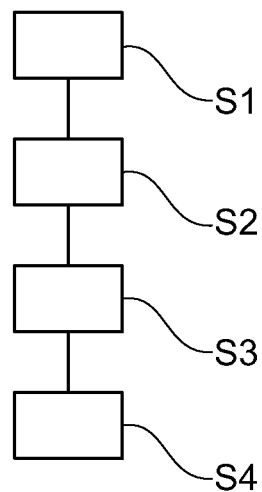
FIG. 6 shows a method of measuring a compression depth according to one aspect of the invention.

FIG. 6 shows a method of measuring a compression depth according to one aspect of the invention, with reference to FIGS. 3 and 4.

In a first step S1, the first pressure transducer 330, which is attached to the monitor 360, measures a liquid pressure in the first liquid filled lumen 320. The first fixed lumen end 321 is attached to the first pressure transducer 330 and the first movable lumen end 322 is attached to the compression pad and is therefore movable between a first position and a second position, wherein a distance between the first and second position corresponds to the first compression depth.

In a second step S2, the first compression depth is derived, by obtaining the pressure corresponding to the measured liquid pressure.

In a third step S3, the second fixed lumen end 351 is attached to the second pressure transducer 340 and the second movable lumen end 352 is attached to the mattress below the patient's chest. The second movable lumen end 352 is therefore movable between a third position and a fourth position, during movement of the second movable lumen end between the third and the fourth positions, corresponding to a moving height. The second pressure transducer 340 therefore measures a pressure corresponding to a moving mattress height by measuring a liquid pressure in lumen 350.

In a fourth step S4, a difference between the first compression depth and the moving mattress height is derived. The difference is shown on FIG. 5*c*, with the alternating component 3500. This alternating component provides information on the absolute chest compression depth. The initial continuous component 3001 provides information on the chest thickness and the drift component 3002 of the difference between transducer 330 and 340 gives information on chest molding.

Preferably, the position of the first movable lumen end 321 and/or of the second movable lumen end 351 are calibrated before a first compression. Preferably the calibration corresponds to the setting of a zero level, at the start of the resuscitation. The calibration may be performed once. Alternately, the calibration may be triggered on a signal such as a force sensor signal.

The person skilled in the art will therefore recognized that the compression sensor can be used not only to measure a compression depth but also to derive an absolute position of the first movable lumen end 322 and/or of the second movable lumen end 352. If the first movable lumen end 322 and/or the second movable lumen end 352 is fixed on a compression pad, an absolute position of the compression pad can be obtained.

The invention claimed is:

1. A compression depth sensor for measuring a compression depth of a patient's chest during CPR, the sensor comprising:
    a first pressure transducer, attachable to a fixed element; and
    a first liquid filled lumen having (i) a first fixed lumen end attachable to the first pressure transducer and (ii) a first movable lumen end being movable between a first position (Pr) and a second position (Pc), wherein a distance between the first and second position defines the compression depth (h),
whereby the first pressure transducer is adapted to measure the compression depth by measuring a change in liquid pressure in the first liquid filled lumen in response to movement of the first movable lumen end between the first position and the second position, the compression depth sensor further comprising:
    a second liquid filled lumen, having a second fixed lumen end attachable to the first pressure transducer and a second movable lumen end being movable between a third position (Prm) and a fourth position (Pcm), wherein a distance between the third and fourth positions defines a moving height (hm), wherein the first pressure transducer comprises a differential pressure transducer adapted to measure an absolute compression depth between the first movable lumen end and the second movable lumen end by measuring a differential liquid pressure between the first liquid filled lumen and the second liquid filled lumen in response to movement of the first movable lumen end and the second movable lumen end, the first pressure transducer being adapted to derive a differential pressure resulting from changes in liquid pressures in the first and second liquid filled lumens.

2. The compression depth sensor according to claim 1, wherein the first movable lumen end comprises a first fixation member, wherein the first fixation member is configured to enable the first movable lumen end to attach to a first movable element.

3. The compression depth sensor according to claim 2, wherein the second movable lumen end comprises a second fixation member, wherein the second fixation member is configured to enable the second movable lumen end to attach to a mattress located below the patient.

4. The compression depth sensor according to claim 1, wherein the first pressure transducer comprises a strain gage transducer or a tip pressure transducer.

5. A method of measuring a compression depth during Cardio Pulmonary Resuscitation (CPR) using the compression depth sensor according to claim 1, the method comprising:
    attaching the first movable lumen end of the first liquid filled lumen to a first movable element disposed on a patient's chest; and
    measuring, via the first pressure transducer, the compression depth experienced by the patient's chest during CPR, wherein the first pressure transducer measures the compression depth by measuring a change in liquid pressure in the first liquid filled lumen in response to movement of the first movable lumen end between the first position and the second position.

6. A Cardio Pulmonary Resuscitation (CPR) apparatus, comprising:
    the compression depth sensor according to claim 2, wherein the first movable element comprises a compression pad.

7. The Cardio Pulmonary Resuscitation (CPR) apparatus according to claim 6, wherein the compression depth sensor is adapted to derive an absolute position difference of the compression pad with respect to an initial position of the compression pad on the patient's chest during CPR.

8. A method for measuring a compression depth (h) of a patient's chest during CPR, the method comprising:
    measuring, by a first pressure transducer, attachable to a fixed element, a change in a first liquid pressure in a first liquid filled lumen, said first liquid filled lumen having (i) as first fixed lumen end attachable to the first pressure transducer and (ii) a first movable lumen end being movable between a first position (Pr) and a second position (Pc), in response to movement of the first movable lumen end between the first position and the second position, wherein a distance between the first and second position corresponds to the compression depth (h); and
    measuring, by the first pressure transducer, a differential pressure corresponding to an absolute compression depth by measuring said first liquid pressure and a second liquid pressure in a second liquid filled lumen, said second liquid filled lumen having (i) a second fixed lumen end attachable to said first pressure transducer and (ii) a second movable lumen end being movable between a third position (Prm) and a fourth position (Pcm), in response to movement of the second movable lumen end between the third and the fourth positions.

9. The method according to claim 8, further comprising: deriving a difference between the compression depth (h) and the moving height (hm).

10. The method according to claim 8, further comprising: measuring chest height and molding effects by measuring a DC component of the differential pressure.

11. The method according to claim 8, further comprising: positioning the first movable lumen end on a contact pad and positioning the second movable lumen end below the patient's chest.

12. The method according to claim 8, further comprising: calibrating a position of at least one of (i) the first movable lumen end and (ii) the second movable lumen end before a first compression.

* * * * *